(12) United States Patent
Jamison et al.

(10) Patent No.: US 10,989,646 B1
(45) Date of Patent: Apr. 27, 2021

(54) REAL TIME MAGNETIC PROPERTIES OF DRILL CUTTINGS, DRILLING FLUIDS, AND SOILS

(71) Applicant: Halliburton Energy Services, Inc., Houston, TX (US)

(72) Inventors: Dale E. Jamison, Houston, TX (US); Daniel Joshua Stark, Houston, TX (US); Marek Kozikowski, Conroe, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/880,711

(22) Filed: May 21, 2020

(51) Int. Cl.
| | |
|---|---|
| E21B 49/00 | (2006.01) |
| G01N 15/06 | (2006.01) |
| G01N 33/28 | (2006.01) |
| G01N 15/00 | (2006.01) |
| E21B 21/06 | (2006.01) |

(52) U.S. Cl.
CPC ....... G01N 15/0656 (2013.01); E21B 49/005 (2013.01); G01N 33/2823 (2013.01); *E21B 21/065* (2013.01); *G01N 2015/0053* (2013.01); *G01N 2015/0693* (2013.01)

(58) Field of Classification Search
CPC .......... G01N 15/0656; G01N 33/2823; G01N 2015/0053; G01N 2015/0693; E21B 49/005; E21B 21/065
USPC .... 324/204, 244.1, 260, 323, 324, 376, 377; 73/152.01–152.04, 152.43, 152.54, 865.8, 73/866; 175/40, 46, 50
See application file for complete search history.

(56) References Cited

U.S. PATENT DOCUMENTS

| | | | |
|---|---|---|---|
| 3,728,613 A * | 4/1973 | Hearn | G01R 33/26 324/301 |
| 3,831,082 A | 8/1974 | Mazzagatti | |
| 4,656,422 A * | 4/1987 | Vail, III | G01R 33/022 324/303 |
| 6,825,657 B2 | 11/2004 | Kleinberg et al. | |
| 7,439,743 B2 | 10/2008 | Potter | |

(Continued)

FOREIGN PATENT DOCUMENTS

| | | |
|---|---|---|
| CN | 206546345 | 10/2017 |
| JP | 6238425 | 11/2017 |

(Continued)

OTHER PUBLICATIONS

Ivakhnenko et al. Magnetic susceptibility of petroleum reservoir fluids, Physics and Chemistry of the Earth, Parts A/B/C, vol. 29, Issues 13-14, 2004, pp. 899-907.

(Continued)

*Primary Examiner* — Robert R Raevis
(74) *Attorney, Agent, or Firm* — Tenley Krueger; C. Tumey Law Group PLLC (57) ABSTRACT

Systems and methods of the present disclosure generally relate to real time characterization of material recovered from a subterranean formation, based on magnetic properties. A system comprises an enclosure comprising electromagnetic shielding; an optically pumped magnetometer (OPM) disposed within the enclosure; and a sample conduit extending into the enclosure, the sample conduit configured to receive a subterranean material recovered from a wellbore, the OPM configured to detect a magnetic response of the subterranean material.

20 Claims, 5 Drawing Sheets

(56) References Cited

U.S. PATENT DOCUMENTS

| | | |
|---|---|---|
| 8,729,886 B2 | 5/2014 | Yang |
| 2005/0017715 A1 | 1/2005 | Prammer et al. |
| 2010/0327869 A1* | 12/2010 | Kim .................. G01N 27/76 |
| | | 324/309 |
| 2012/0013335 A1 | 1/2012 | Saasen et al. |
| 2012/0273193 A1* | 11/2012 | Sen .................. G01N 24/081 |
| | | 166/250.01 |
| 2013/0234702 A1* | 9/2013 | Blanz .................. G01R 33/26 |
| | | 324/301 |
| 2013/0265043 A1 | 10/2013 | Nicot et al. |
| 2018/0003786 A1 | 1/2018 | Washburn |
| 2018/0203151 A1 | 7/2018 | Kouchmeshky et al. |
| 2019/0360326 A1 | 11/2019 | Deville et al. |

FOREIGN PATENT DOCUMENTS

| | | |
|---|---|---|
| WO | 2009-079054 | 6/2009 |
| WO | 2013162400 | 10/2013 |

OTHER PUBLICATIONS

International Search Report for Application No. PCT/US2020/035119, dated Feb. 2, 2021.

* cited by examiner

REAL TIME MAGNETIC PROPERTIES OF DRILL CUTTINGS, DRILLING FLUIDS, AND SOILS

BACKGROUND

During drilling of a wellbore into a subterranean formation, drilling fluid may be circulated from the surface, into the wellbore, and back up to the surface. The drilling fluid serves several functions, such as transporting drill cuttings to the surface for separation from the drilling fluid. Additionally, other solids present in the wellbore may be circulated to the surface. Determining content of the drill cuttings recovered from the wellbore may be useful for managing an efficient drilling operation.

BRIEF DESCRIPTION OF THE DRAWINGS

These drawings illustrate certain aspects of some examples of the present invention and should not be used to limit or define the invention.

DETAILED DESCRIPTION

Systems and methods of the present disclosure generally relate to a characterization of mineralogy of recovered subterranean material in real time. Magnetic susceptibility of the recovered subterranean material may be utilized to determine physical properties of the drilled formation to manage operational conditions and/or drilling fluid composition, to mitigate potential operative risks. Specifically, the systems and methods of the present disclosure may employ an optically pumped magnetometer ("OPM") to characterize the mineralogy of the recovered subterranean material to anticipate wellbore problems, control a composition of a drilling fluid, and/or manage operational or drilling conditions to minimize non-productive time risk.

In some examples, the systems and methods of the present disclosure may measure a low-gravity-solids ("LGS") content of drilling fluid, in real time, to manage product addition to control rheology and wellbore pressure, such as equivalent circulating densities ("ECD"). As used herein, the term low-gravity solids or LGS refers to solids having a specific gravity of about 2.7 or less (e.g., 2.6 to 2.7, or 2.0 to 2.7).

In other examples, the systems and methods of the present disclosure may also quantitatively measure, in real time, iron particulates in the drilling fluid to provide a sense of casing wear, as well as provide information to manage lubricant additives in the drilling fluid, for example. In some cases, this may help to manage operational parameters such as weight on bit ("WOB") and the resultant changes in casing wear.

Additionally, the systems and methods of the present disclosure may pair well with real time drilling fluids graphics software and/or measurement-while-drilling ("MWD") tools to provide a more complete picture of active drilling to improve characterization of a subterranean formation and determine potential production or decline characteristics. In addition to improving a characterization of components of rocks of the subterranean formations, examples of the present disclosure may also improve drilling fluid formulation and/or management of fluid properties in real time.

Figure 1:
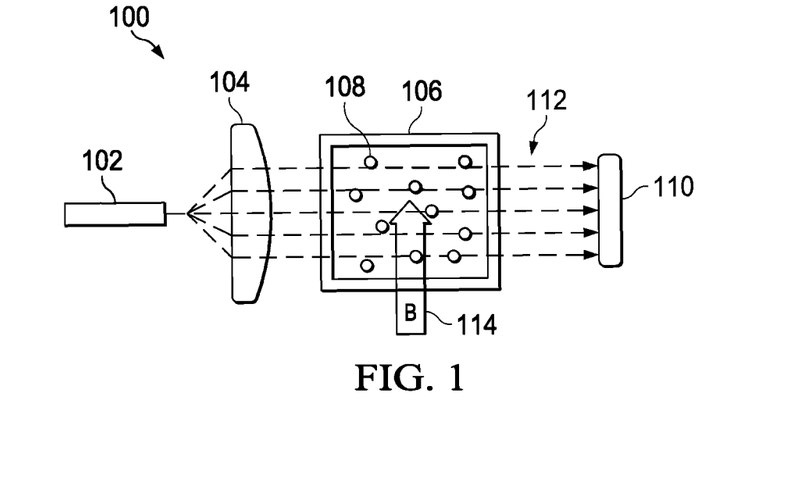
FIG. 1 illustrates an optically pumped magnetometer ("OPM"), in accordance with particular examples of the present disclosure.

FIG. 1 illustrates an optically pumped magnetometer ("OPM") 100 in accordance with particular examples of the present disclosure. The OPM 100 may include a laser 102 disposed adjacent to a lens 104. The lens 104 may be disposed between the laser 102 and a cell 106. The cell 106 may be a glass vapor cell containing rubidium atoms 108. The cell 106 may be disposed between the lens 104 and a photo detector 110. The laser 102 may emit light, via light paths 112, through the cell 106 and to the photo detector 110. The OPM 100 is a non-limiting example of an OPM, and other suitable OPMs may be utilized, as should be understood by one having skill in the art, with the benefit of this disclosure.

A magnetic field 114 may vary a magnetic response of the OPM 100. When a magnetic field 114 (e.g., the background magnetic field) is equal to zero, the rubidium atoms 108 become largely transparent. When the magnetic field 114 is not zero, the magnetic field 114 may extend in a direction perpendicular to the light paths 112 to cause the rubidium atoms 108 to absorb more light. The photo detector 110 senses this change in transparency and produces an electric current proportional to light transmitted through the cell 106. Thus, a magnetic signal is converted to an electric signal via the OPM 100.

Magnetic susceptibility properties may be used in stratigraphic core correlation methods using wireline tools. The magnetic susceptibilities may vary an OPM response. These methods may be used for iron ore and diamond exploration. Magnetic susceptibility analysis may be used on soils, rocks, powders, and liquids. In oilfield applications, a permeability of subterranean formations may be successfully characterized using magnetic susceptibility. These properties may be useful in real time drilling for preventative interpretation of data from a geomechanics and operational condition perspective. Table 1 lists magnetic susceptibility for various rocks, minerals, and soils.

TABLE 1

| Magnetic Susceptibility of Minerals. | |
|---|---|
| Mineral | Magnetic Susceptibility, $10^8 \chi/m^3 kg^{-1}$ |
| Barite | — |
| Water | −0.90 |
| Quartz | −0.58 |
| Orthoclase, calcite | −0.48 |
| Dolomite | 1.1 |
| Muscovite | 1 to 15 |
| Biotite | 15 to 65 |
| Amphiboles | 16 to 69 |
| Pyroxenes | 4 to 94 |
| Epidote | 25 to 31 |
| Kaolinite | −1.9 |

TABLE 1-continued

Magnetic Susceptibility of Minerals.

| Mineral | Magnetic Susceptibility, $10^8\ \chi/m^3 kg^{-1}$ |
|---|---|
| Montmorillonite | 2.7 |
| Bentonite | 5.8 |
| Nontronite | 86.3 |
| Vermiculite | 15.2 |
| Prochlorite | 15.7 |
| Attapulgite | 2.0 |

In some configurations, a mud or drill cutting sample may cause the magnetic field 114 to van the OPM response if the material is placed in the proximity of the magnetic field 114. The change in the OPM response may be due to magnetic properties of the sample and may be correlated to known sample materials. For example, bentonite responds differently than limestone. Real time measurements of the magnetic susceptibility when analyzed with real time logging data, initial seismic data, and basin modeling may provide a valuable insight into potential geo-mechanic issues and operational problems while drilling. Additionally, the results may provide casing wear data that may help to reduce casing failures as well as provide insight for lubricant product additions.

In some examples, the OPM 100 may be utilized to determine an LGS content of a material. Correlations between a density of the material and its magnetic susceptibility, and a type of formation being drilled, may be utilized to provide the LGS content, as should be understood by one having skill in the art with the benefit of this disclosure. For example, the LGS content may be determined or inferred because barite (e.g., see Table 1) has no impact on the magnetic susceptibility. Table 2 lists densities for various minerals.

TABLE 2

Densities of Minerals.

| Mineral | Density, g/cm$^3$ |
|---|---|
| Barite | 4.5 |
| Chalcopyrite | 4.2 |
| Pyrite | 5.0 |
| Pyrrhotite | 4.6 |
| Sphalerite | 4.0 |
| Galena | 7.5 |
| Magnetite | 5.2 |
| Hematite | 5.3 |

Figure 2A:
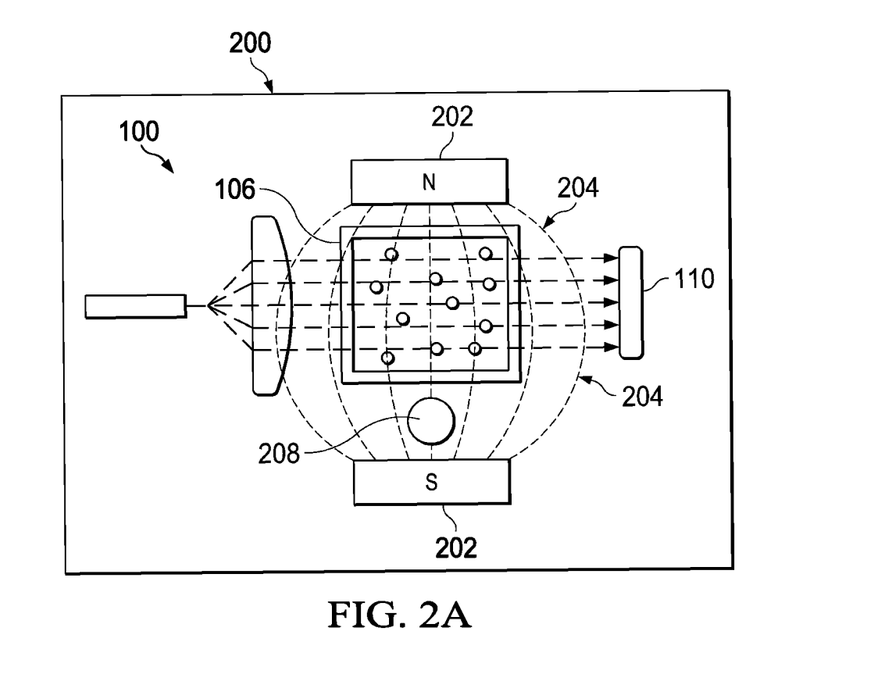
FIG. 2A illustrates the OPM adjacent to a non-rotating subterranean sample, in accordance with particular examples of the present disclosure.

FIG. 2A illustrates the OPM 100 adjacent to a recovered subterranean material 208, in accordance with particular examples of the present disclosure. As illustrated, the OPM 100 may be placed in magnetic isolation with an enclosure 200. In certain examples, the enclosure 200 is electromagnetic shielding and may be made of a metal sheet or a metal screen, for example. The cell 106 may be disposed adjacent to and/or between magnetic devices 202. The magnetic devices 202 may include a permanent magnet, electromagnet, and/or Helmholtz coil.

The magnetic field 204 may be generated with the magnetic devices 202 or other electromagnet arrangements. In some configurations, the magnetic field 204 may be modulated. There may be one or more magnetic fields 204, in some examples. The magnetic field 204 may be configured as a high intensity or a low intensity magnetic field. For example, the low intensity magnetic field may be a linear region of the material and may include a range of up to a few hundred Gauss. The high intensity magnetic field may be a field where magnetic saturation has occurred and remanence (or residual magnetism) is in place. Depending on the material type and size, the high magnetic field may include a range of up to a few thousand Gauss (e.g., 3,500 Gauss for ferrite and 10,000 Gauss for neodymium). The high intensity magnetic field may be used to set a standard orientation for magnetic fields within the material, with a low probe used to create perturbations to the material's orientation to determine a response.

A recovered subterranean material 208 may be inserted between the cell 106 and the magnetic devices 202. The recovered subterranean material 208 may include drill cuttings and/or whole mud, for example. The recovered subterranean material 208 may be exposed to the magnetic field 204 and cause the magnetic field 204 to vary a magnetic response of the OPM 100, similar to the magnetic field 114, as described with reference to FIG. 1, for example. The magnetic response of the OPM 100 may be caused by a change in light intensity or transparency that is measured by the photo detector 110 of the OPM 100, as described with reference to the rubidium atoms 108 of FIG. 1, for example. As noted previously, the change in the OPM response may be correlated to known sample materials to determine content of the recovered subterranean material 208.

If the recovered subterranean material 208 is likely to be ferromagnetic or have some form of magnetic hysteresis, the recovered subterranean material 208 may be pulsed with a high intensity magnetic field 204 before being brought to the OPM 100, in some examples.

Figure 2B:
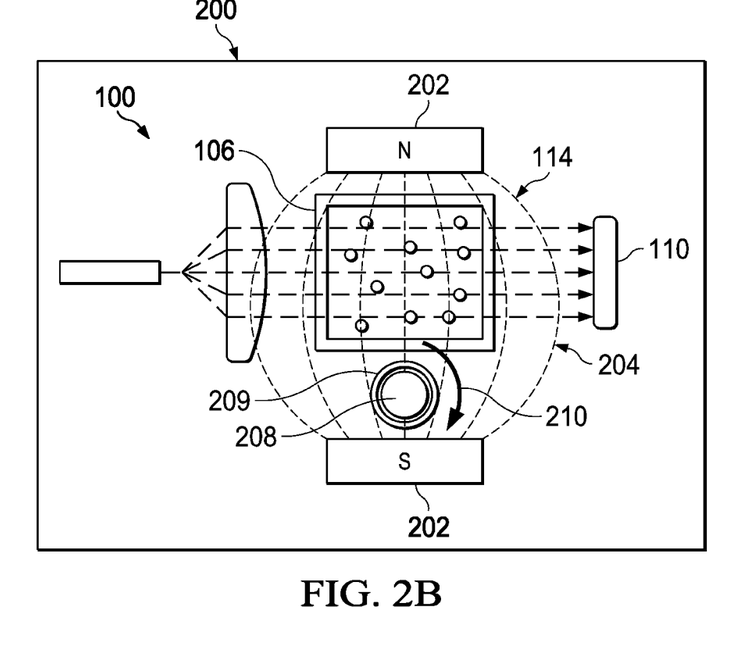
FIG. 2B illustrates the OPM adjacent to a rotating subterranean sample in accordance with particular examples of the present disclosure.

FIG. 2B illustrates the OPM 100 adjacent to the recovered subterranean material 208 that is in rotation, in accordance with particular examples of the present disclosure. As illustrated, the OPM 100 may be placed in magnetic isolation with the enclosure 200. The cell 106 may be disposed adjacent and/or between the magnetic devices 202. The magnetic devices 202 may include a permanent magnet, electromagnet, and/or Helmholtz coil, for example. As noted above, the magnetic field 204 may be configured as a high intensity or a low intensity magnetic field.

The recovered subterranean material 208 may be inserted between the cell 106 and the magnetic devices 202. The recovered subterranean material 208 may include drill cuttings and/or whole mud, for example. The recovered subterranean material 208 may be exposed to the magnetic field 204 and cause the magnetic field 204 to vary a magnetic response of the OPM 100, as the recovered subterranean material 208 is rotated. This magnetic response may be caused by a change in light intensity or transparency that is measured by the photo detector 110 of the OPM 100. The recovered subterranean material 208 may be rotated as indicated by arrow 210. Rotation may occur via any suitable means, such as, for example, the recovered subterranean material 208 may be placed within a sample chamber or conduit 209. The sample chamber or conduit 209 may be rotatable. In some examples, the sample chamber or conduit 209 may be operatively coupled to a motor (not shown). The sample chamber or conduit 209 may be made of non-ferromagnetic materials, for example, such as austenitic steel, to allow the magnetic field 204 to penetrate and pass through the sample chamber or conduit 209 to contact the recovered subterranean material 208, for example.

Figure 3:
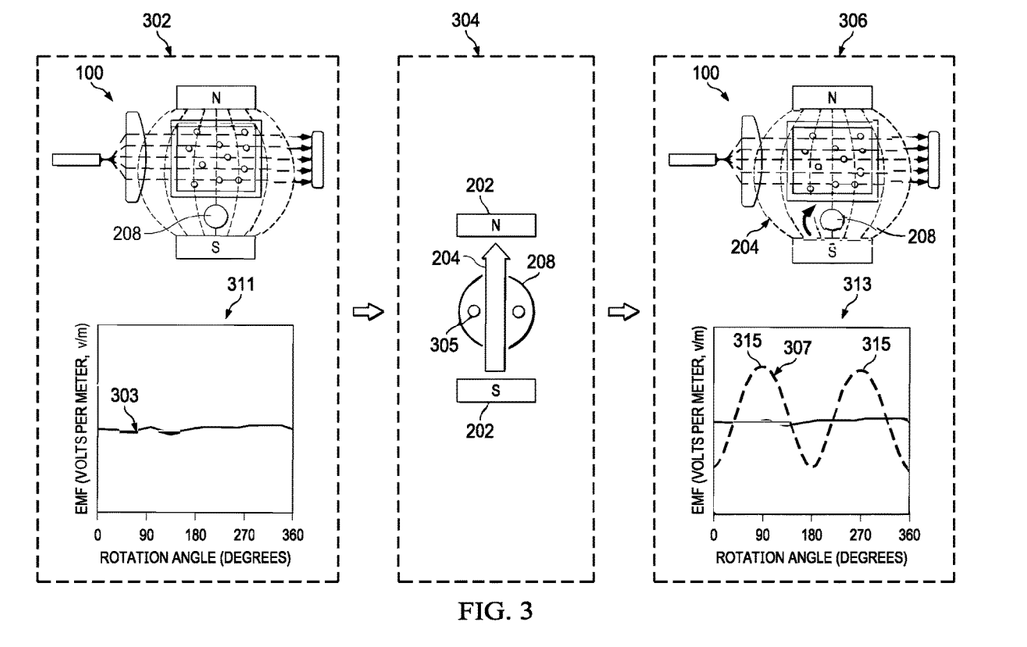
FIG. 3 illustrates an exemplary method to determine magnetic particle content of a recovered subterranean material, in accordance with particular examples of the present disclosure.

FIG. 3 illustrates an exemplary method 300 to determine magnetic particle content of the recovered subterranean material 208, in accordance with particular examples of the present disclosure. Magnetic susceptibility of the recovered subterranean material 208 may be used to determine a concentration and build-up of metal fines. The recovered subterranean material 208 may be initially unaltered (e.g., not magnetized by an external source such as the magnetic devices 202 shown on FIG. 2A). The recovered subterranean material 208 may be rotated.

A magnetic response 303 caused by the recovered subterranean material 208 may be determined by the OPM 100 at stage 302. For example, a rotation angle of the recovered subterranean material 208 may be plotted against an electromagnetic field strength (EMF) of the recovered subterranean material 208, as shown on a graph 311, for example. As shown on the graph 311, the EMF varies slightly with the rotation, when the recovered subterranean material 208 is unaltered.

After initially measuring of the magnetic response 303 of the recovered subterranean material 208 in an unaltered state, wear particles 305 in the recovered subterranean material 208 may be magnetized or altered with the magnetic devices 202, via the magnetic field 204, at stage 304, for example. The wear particles 305 may include metal that has broken off from downhole components, such as casing, for example.

Subsequently, a magnetic response 307 caused by the recovered subterranean material 208 while the recovered subterranean material 208 is rotating may be determined by the OPM 100, at stage 306, for example. A rotation angle of the recovered subterranean material 208 may be plotted against the EMF of the recovered subterranean material 208, as shown on a graph 313, for example.

As shown on the graph 313, the EMF varies substantially, as shown at peaks 315, for example. A magnitude of a peak-to-peak magnetometer response may be calibrated to a magnetic particle content. Thus, a quantitative concentration of the wear particles 305 may be determined. In some cases, the recovered subterranean material 208 may be taken from a mud pit and/or flow line to determine a change in wear particle concentration with respect to time based on current drilling conditions, such as ROP and WOB, for example. The concentrations with respect to time may be recorded thereby allowing a model to be developed to determine the highest probable wear locations (e.g., of a downhole tubular such as casing) downhole based on high stress contact points due to well trajectory and operating conditions. Thus, using these data, casing failure may be anticipated and avoided with proper application of friction reducing additives and optimized operating parameters, for example.

In certain examples, when a viscosity of the recovered subterranean material 208 containing the magnetic or wear particles 305 is below a desired of threshold amount, the wear particles 305 may be fixed (or have their rotation greatly retarded) either through adding a viscosifier (e.g., a clay) or by using an adhesive to collect the wear particles 305 at the end of a flow line, for example.

Figure 4:
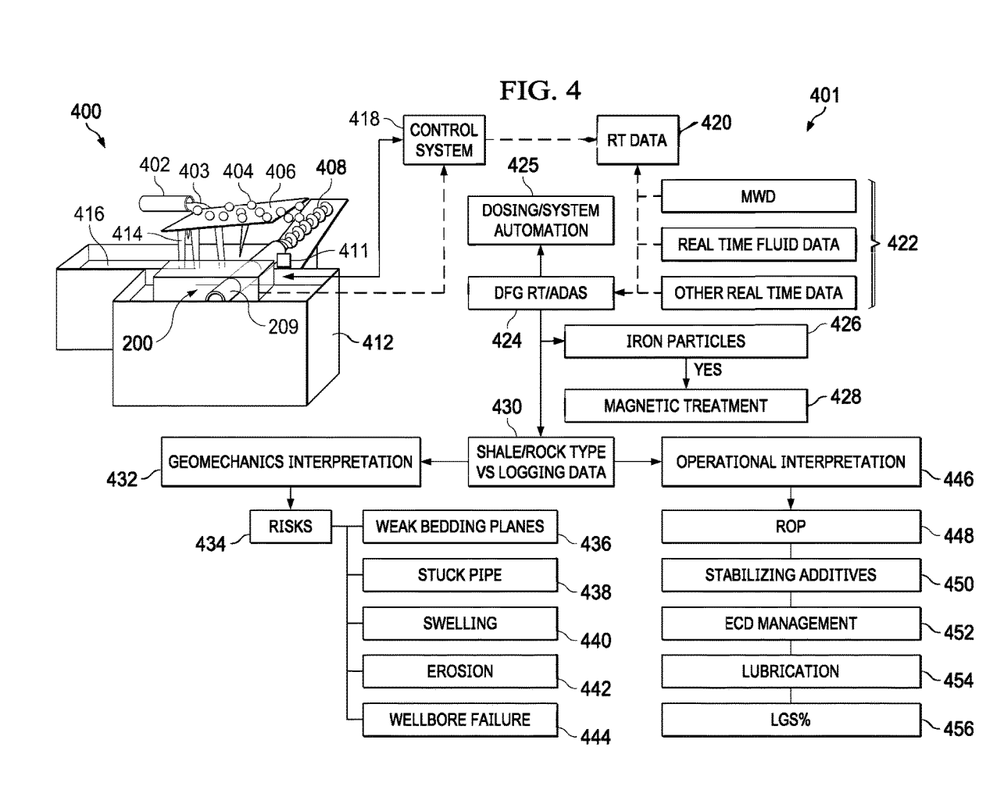
FIG. 4 illustrates a system including the OPM and a workflow thereof, in accordance with particular examples of the present disclosure.

FIG. 4 illustrates a system 400 including the enclosure 200 and a workflow 401 thereof, in accordance with particular examples of the present disclosure. The OPM 100 (e.g., shown on FIGS. 2A and 2B) and associated components (e.g., the magnetic devices 202 shown on FIGS. 2A and 2B) may be disposed within the enclosure 200. The system 400 may be utilized to analyze recovered downhole material according to the workflow 401. The workflow 401 correlates real time drilling data to lag time source position of drill cuttings 404 and their measured mineralogy by magnetic susceptibility as determined by the OPM 100.

The system 400 may also include a flow line 402 discharging a downhole fluid 403 including whole mud 414 and the drill cuttings 404 onto a solids control device 406. The drill cuttings 404 may be gathered by an auger 408 and transferred through the sample conduit 209 into a drill cuttings box 412. The whole mud 414 separated via the solids control device 406 may flow into a mud pit 416.

The sample conduit 209 may extend through the enclosure 200 and may be mechanically coupled (e.g., via a gear or shaft) to a motor 411 that may be utilized to rotate the sample conduit 209. The sample conduit 209 may extend adjacent to the OPM 100 and may pass between the magnetic devices 202.

The solids control device 406 may include one or more of a shaker (e.g., shale shaker), a centrifuge, a hydro-cyclone, a separator (including magnetic and electrical separators), a de-silter, a de-sander, a separator, a filter (e.g., diatomaceous earth filters), a heat exchanger, and any fluid reclamation equipment. The solids control device 406 may remove and separate recovered solids (e.g., the drill cuttings 404) from the circulated drilling fluid (e.g., the downhole fluid 403). After such removal, a clean drilling fluid (e.g., the whole mud 414) may be transported to the mud pit 416 or for further downstream processing.

The system 400 may further include a system controller 418 (e.g., a programmable logic controller) that is in communication (e.g., wire or wireless) with the system 400 to operate or control the system 400. The system controller 418 may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. The system controller 418 may be any processor-driven device, such as, but not limited to, a personal computer, laptop computer, smartphone, tablet, handheld computer, dedicated processing device, and/or an array of computing devices. In addition to having a processor, the system controller 418 may include a server, a memory, input/output ("I/O") interface(s), and a network interface. The memory may be any computer-readable medium, coupled to the processor, such as RAM, ROM, and/or a removable storage device for storing data and a database management system ("DBMS") to facilitate management of data stored in memory and/or stored in separate databases. The system controller 418 may also include display devices such as a monitor featuring an operating system, media browser, and the ability to run one or more software applications. Additionally, the system controller 418 may include non-transitory computer-readable media. Non-transitory computer-readable media may include any instrumentality or aggregation of instrumentalities that may retain data and/or instructions for a period of time.

The workflow 401 may include geo-mechanic and operational interpretation of real time data utilizing drilling fluids graphic software ("DFG") and real time distributed acoustic sensing ("DAS") data, to mitigate risk and improve drilling optimization. DFG may include a hydraulics modeling program that accurately accounts for the effects of drilling fluid compressibility and thermal expansion on fluid density, including the reduction in temperature while the drilling fluid, such as mud, returns to the surface that causes an increase in density, viscosity, and rheological properties. DAS may utilize Rayleigh scattering principles to determine acoustic strain signals over long distances, effectively turning the optic fiber cable into a series of virtual microphones. Once the data is acquired, advanced processing techniques such as frequency filtering, and time and depth domain stacking may be applied to obtain information for a wide variety of applications.

The workflow 401 may include acquiring real time data 420. The real time data 420 may include data acquired with the OPM 100 such as magnetic particle measurements of the drill cuttings 404, for example. The workflow 401 may also utilize real time data 422 that may be acquired from a downhole instrument such as with an MWD tool.

The real time data 422 may include formation, rheology, and fluid properties, for example. The real time data 420 may be utilized with the real time data 422 along with DFG and DAS data (collectively referred to as "DFGDAS 424"), to determine dosing or system automation 425. The dosing or system automation 425 may include adjusting (e.g., improving) drilling fluid formulation and management of fluid properties in real time, for example.

The real time data 420 and 422 along with the DFGDAS 424 may be utilized for an iron-particles determination 426 of iron particles that are present in the drill cuttings 404 and/or the whole mud 414. If the iron particles are present in an amount greater than a desired or threshold amount, then magnetic treatment 428 of the drill cuttings 404 may occur, such as removal of the iron particles from the drill cuttings 404 and/or the whole mud 414 with a magnet and/or adhesive, for example. The iron particles 426 in the drilling cuttings 404 and/or the whole mud 414 may be quantitatively measured to provide a sense of casing wear as well as providing information to manage lubricant additives in the drilling fluid. In some cases, this may help to manage operational parameters such as WOB and the resultant changes in the casing wear.

Additionally, the real time data 420 and 422 may be used in concert to determine correlations 430 between rock type and logging data. Correlations 430 may allow for geomechanic interpretation 432 including risks 434. The risks 434 may include weak bedding planes 436, stuck pipe 438, swelling 440, erosion 442, and/or wellbore failure 444, for example. The correlations 430 may also be utilized for operational interpretation 446 which may include rate of penetration ("ROP") 448, stabilizing additives 450 (e.g., a shale stabilizer), ECD management 452, lubrication 454 (e.g., lubricants such as a polymer), and/or an LGS percentage 456, for example.

Figure 5:
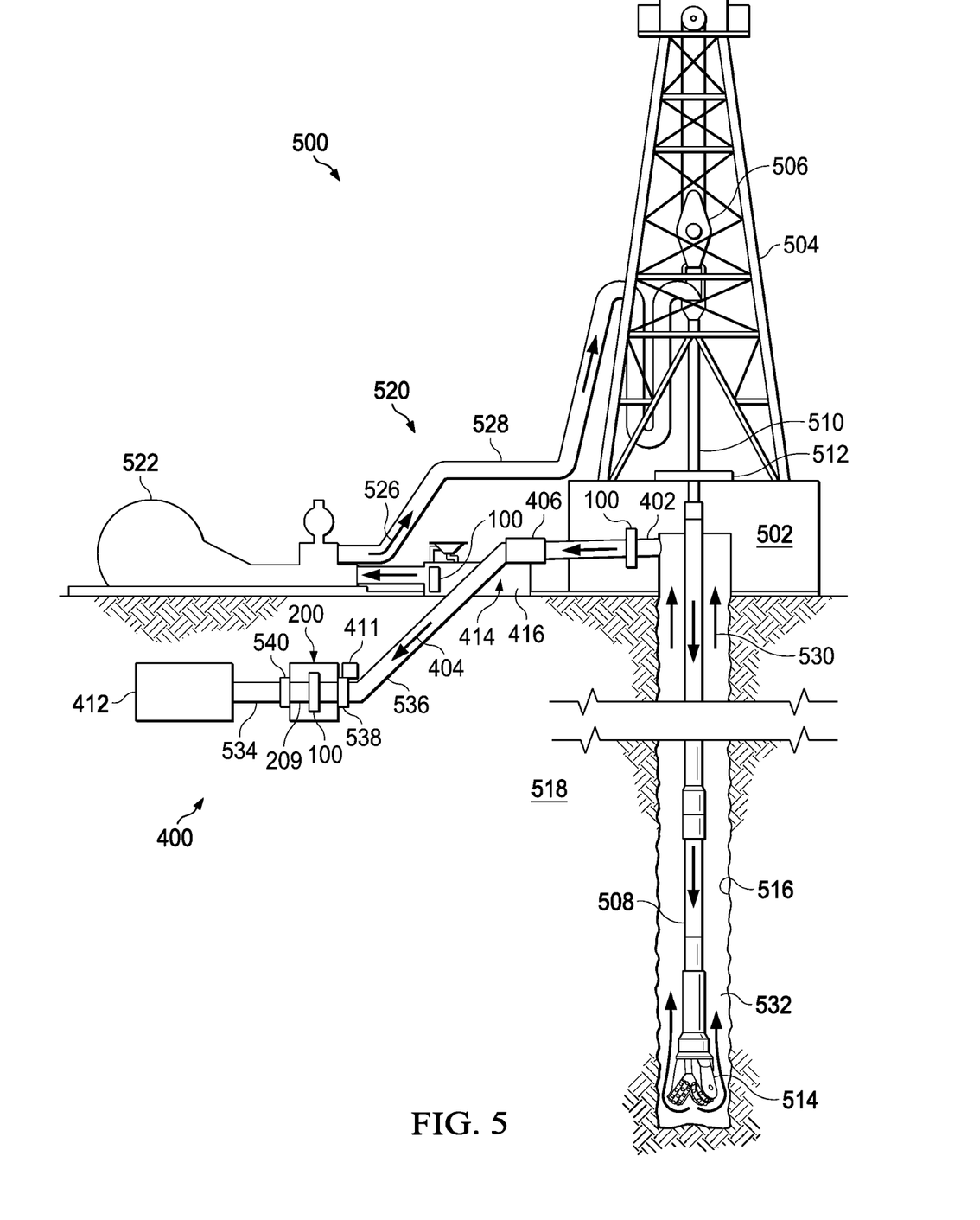
FIG. 5 is a schematic diagram of an exemplary drilling system with the OPM, in accordance with particular examples of the present disclosure.

FIG. 5 illustrates a drilling system 500 including the system 400 and the workflow 401 (e.g., shown on FIG. 4) in accordance with particular examples of the present disclosure. It should be noted that while FIG. 5 depicts a land-based drilling system, those skilled in the art will readily recognize that the principles described herein are equally applicable to subsea drilling operations that employ floating or sea-based platforms and/or rigs, without departing from the scope of the present disclosure.

As illustrated, the drilling system 500 may include a drilling platform 502 that supports a derrick 504 having a traveling block 506 for raising and lowering a drill string 508. The drill string 508 may include, but is not limited to, drill pipe and coiled tubing, as generally known to those skilled in the art. A top drive or kelly 510 may support the drill string 508. The drill string 508 may be lowered through a rotary table 512, in some examples. A drill bit 40 may be attached to the distal end of the drill string 508 and may be driven either by a downhole motor and/or via rotation of the drill string 508 from the well surface. Without limitation, the drill bit 40 may include, roller cone bits, PDC bits, natural diamond bits, any hole openers, reamers, coring bits, and the like. As the drill bit 40 rotates, it may create a wellbore 516 that penetrates a subterranean formation 518.

The drilling system 500 may further include a fluid monitoring and handling system 520 comprising component parts such as a mud pump 522, a solids control device 406, and a mud pit 416. The mud pump 522 may include any conduits, pipelines, trucks, tubulars, and/or pipes used to convey clean drilling fluid 526 downhole. The mud pump 522 may also include any pumps, compressors, or motors (e.g., surface or downhole) used to move the clean drilling fluid 526, as well as any valves or related joints used to regulate the pressure or flowrate of the clean drilling fluid 526, and any sensors (e.g., pressure, temperature, flow rate), gauges, or combinations thereof, for example.

The mud pump 522 may circulate the clean drilling fluid 526 through a feed pipe 528 and to the top drive or kelly 510, which may convey the clean drilling fluid 526 downhole through the interior of the drill string 508 and through one or more orifices in the drill bit 40. The now circulated drilling fluid 530 may then be circulated back to the surface via an annulus 532 defined between the drill string 508 and the walls of the wellbore 516. At the surface, the circulated drilling fluid 530 may be conveyed to the solids control device 406 via an interconnecting flow line 402. The solids control device 406 may include one or more of a shaker (e.g., shale shaker), a centrifuge, a hydro-cyclone, a separator (including magnetic and electrical separators), a de-silter, a de-sander, a separator, a filter (e.g., diatomaceous earth filters), a heat exchanger, and any fluid reclamation equipment, as previously described in FIG. 4. The solids control device 406 may remove and separate recovered solids (e.g., the drill cuttings 404) from the circulated drilling fluid 530. After passing through the solids control device 406, a clean drilling fluid 526 may move into a nearby mud pit 416.

The fluid monitoring and handling system 520 may further include the system 400 or components thereof and the corresponding workflow 401, as described in FIG. 4. As illustrated in FIG. 5, the system 400 may be disposed on or adjacent to the platform 502. The system 400 is in fluid communication with the solids control device 406 via conduit 536 to receive recovered solids or the drill cuttings 404. The conduit 536 may be rotatably coupled to the sample conduit 209 via a swivel joint 538, for example.

The drill cuttings 404 may move through the sample conduit 209 passing adjacent to the OPM 100 which may be disposed within the enclosure 200, as described in FIGS. 2A and 2B, for example. The drill cuttings 404 may pass through the sample conduit 209 into the drill cuttings box 412 via conduit 534 for disposal or further processing. The sample conduit 209 may be rotatably coupled to the conduit 534 via a swivel joint 540, for example. The sample conduit 209 may rotate periodically or continuously via the motor 411 and the swivel joints 538 and 540, for example. The system 400 may continuously or intermittently measure the magnetic particle content of the recovered solids or the drill cuttings 404, which have been recovered from the circulated drilling fluid 530.

As noted previously, the magnitude of the peak-to-peak magnetic response of the OPM 100 may be calibrated to the magnetic particle content of the drill cuttings 404, as described in FIG. 3. Thus, the quantitative concentration of the wear particles 305 (e.g., shown on FIG. 2B) of the drill cuttings 404 may be determined.

In certain examples, the OPM 100 and associated components (e.g., shown on FIGS. 2A and 2B) may also be positioned at the flow line 402 to measure properties of the drilling fluid 530. In other examples, the OPM 100 and associated components may also be positioned in the mud pit 416 to measure properties of the whole mud 414 (e.g., no drill cuttings 404 present in the whole mud 414) disposed within the mud pit 416, for example. The system 400 may continuously or intermittently measure the magnetic particle content at the flow line 402 and the mud pit 416. The recovered subterranean material 208 (e.g., shown on FIG. 2B) may be taken from the mud pit 416 and/or the flow line 402 to determine the change in wear particle concentration with respect to time based on the current drilling conditions, such as ROP and WOB, for example.

The concentrations with respect to time may be recorded, thereby allowing a model to be developed to determine the highest probable wear locations (e.g., wear locations of a downhole tubular such as casing) downhole based on high stress contact points due to well trajectory and operating conditions. Thus, using these data, casing failure may be anticipated and avoided with proper application of friction reducing additives and optimized operating parameters, for example.

Accordingly, the systems and methods of the present disclosure may utilize an OPM to characterize material recovered from a downhole environment. The systems and methods may include any of the various features disclosed herein, including one or more of the following statements.

Statement 1. A system comprising an enclosure comprising electromagnetic shielding; an optically pumped magnetometer (OPM) disposed within the enclosure; and a sample conduit extending into the enclosure, the sample conduit configured to receive a subterranean material recovered from a wellbore, the OPM configured to detect a magnetic response of a recovered subterranean material.

Statement 2. The system of the statement 1, further comprising magnetic devices disposed within the enclosure, wherein the sample conduit extends between the magnetic devices and is configured for exposure to a magnetic field emitted from the magnetic devices.

Statement 3. The system of the statement 2, wherein the sample conduit is made of a non-ferromagnetic material.

Statement 4. The system of any of the preceding statements, wherein the sample conduit is configured to rotate.

Statement 5. The system of any of the preceding statements, wherein the magnetic devices comprise a permanent magnet, electromagnet, or Helmholtz coil.

Statement 6. The system of any of the preceding statements, further comprising the subterranean material, the subterranean material comprising drill cuttings or whole mud.

Statement 7. The system of any of the preceding statements, wherein the sample conduit passes adjacent to the OPM.

Statement 8. A system comprising an enclosure comprising electromagnetic shielding; an optically pumped magnetometer (OPM) disposed within the enclosure; and a sample conduit passing through the enclosure, the sample conduit in fluid communication with a wellbore, the OPM configured to detect a magnetic response of a subterranean material disposed within the sample conduit.

Statement 9. The system of the statement 8, wherein the sample conduit is configured to rotate.

Statement 10. The system of the statement 8 or 9, comprising the subterranean material, the subterranean material comprising drill cuttings or whole mud, wherein the sample conduit is adjacent to the OPM.

Statement 11. The system of any of the statements 8-10, further comprising magnetic devices, wherein the sample conduit extends between the magnetic devices and is configured for exposure to a magnetic field emitted from the magnetic devices.

Statement 12. The system of any of the statements 8-11, wherein the magnetic devices comprise a permanent magnet, electromagnet, or Helmholtz coil.

Statement 13. The system of any of the statements 8-12, wherein the sample conduit is upstream to a drill cuttings box.

Statement 14. The system of any of the statements 8-13, wherein the sample conduit is downstream to an auger.

Statement 15. A method comprising receiving within a conduit, a subterranean material from a wellbore, the conduit passing through an enclosure comprising magnetic shielding; and receiving the subterranean material adjacent to an optically pumped magnetometer (OPM) and receiving the subterranean material between magnetic devices, the OPM and the magnetic devices disposed within the enclosure.

Statement 16. The method of the statement 15, further comprising measuring a magnetic response of the subterranean material with the OPM.

Statement 17. The method of any of the statements 15-16, further comprising rotating the conduit.

Statement 18. The method of any of the statements 15-17, further comprising measuring a magnetic response of the subterranean material during rotation of the sample conduit.

Statement 19. The method of any of the statements 15-18, further comprising determining an amount of wear particles present in the subterranean material.

Statement 20. The method of any of the statements 15-19, further comprising determining a low gravity solids (LGS) content of the subterranean material.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A system comprising:
an enclosure comprising electromagnetic shielding;
an optically pumped magnetometer (OPM) disposed within the enclosure; and
a sample conduit extending into the enclosure, the sample conduit configured to receive a subterranean material recovered from a wellbore, the OPM configured to detect a magnetic susceptibility of a recovered subterranean material.

2. The system of claim 1, further comprising magnetic devices disposed within the enclosure, wherein the sample conduit extends between the magnetic devices and is configured for exposure to a magnetic field emitted from the magnetic devices.

3. The system of claim 2, wherein the sample conduit is made of a non-ferromagnetic material.

4. The system of claim 3, wherein the sample conduit is configured to rotate.

5. The system of claim 1, further comprising a magnetic device disposed within the enclosure, the magnetic device comprising a permanent magnet, an electromagnet, or a Helmholtz coil.

6. The system of claim 1, further comprising the subterranean material, the subterranean material comprising drill cuttings or whole mud.

7. The system of claim 1, wherein the sample conduit passes adjacent to the OPM.

8. A system comprising:
an enclosure comprising electromagnetic shielding;
an optically pumped magnetometer (OPM) disposed within the enclosure; and
a sample conduit passing through the enclosure, the sample conduit in fluid communication with a wellbore, the OPM configured to detect a magnetic susceptibility of a subterranean material disposed within the sample conduit.

9. The system of claim 8, wherein the sample conduit is configured to rotate.

10. The system of claim 8, further comprising the subterranean material, the subterranean material comprising drill cuttings or whole mud, wherein the sample conduit is adjacent to the OPM.

11. The system of claim 10, further comprising magnetic devices, wherein the sample conduit extends between the magnetic devices and is configured for exposure to a magnetic field emitted from the magnetic devices.

12. The system of claim 8, further comprising a magnetic device disposed within the enclosure, the magnetic device comprising a permanent magnet, an electromagnet, or a Helmholtz coil.

13. The system of claim 8, wherein the sample conduit is upstream to a drill cuttings box.

14. The system of claim 13, wherein the sample conduit is downstream from an auger.

15. A method comprising:
receiving within a conduit, a subterranean material from a wellbore, the conduit passing through an enclosure comprising magnetic shielding;
receiving the subterranean material adjacent to an optically pumped magnetometer (OPM) and receiving the subterranean material between magnetic devices, the OPM and the magnetic devices disposed within the enclosure; and
measuring a magnetic susceptibility of the subterranean material with the OPM.

16. The method of claim 15, further comprising passing the subterranean material through the conduit, the conduit comprising a non-ferromagnetic material.

17. The method of claim 16, further comprising rotating the conduit.

18. The method of claim 15, further comprising rotating the conduit and measuring the magnetic susceptibility of the subterranean material during rotation of the conduit.

19. The method of claim 18, further comprising determining an amount of wear particles present in the subterranean material.

20. The method of claim 19, further comprising determining a low gravity solids (LGS) content of the subterranean material.

* * * * *